(12) United States Patent
Seakins et al.

(10) Patent No.: US 9,555,210 B2
(45) Date of Patent: *Jan. 31, 2017

(54) BREATHING ASSISTANCE APPARATUS

(75) Inventors: Paul John Seakins, Auckland (NZ); Malcolm David Smith, Auckland (NZ); Mohammad Thudor, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 13/540,357

(22) Filed: Jul. 2, 2012

(65) Prior Publication Data

US 2013/0081619 A1    Apr. 4, 2013

Related U.S. Application Data

(60) Continuation of application No. 11/554,792, filed on Oct. 31, 2006, now Pat. No. 8,235,041, which is a (Continued)

(30) Foreign Application Priority Data

Mar. 21, 2000  (NZ) ....................................... 503495

(51) Int. Cl.
 *A61M 16/16*   (2006.01)
 *A61M 16/08*   (2006.01)
 (Continued)

(52) U.S. Cl.
CPC ....... *A61M 16/161* (2014.02); *A61M 16/0003* (2014.02); *A61M 16/08* (2013.01);
(Continued)

(58) Field of Classification Search
CPC .. A61M 16/00; A61M 16/0003; A61M 16/10; A61M 16/1005; A61M 16/1045; A61M 16/1075; A61M 16/108; A61M 16/1085; A61M 16/109; A61M 16/16; A61M 16/161; A61M 2016/102
(Continued)

(56) References Cited

U.S. PATENT DOCUMENTS 485,127 A    10/1892 Lynch
3,582,968 A    6/1971 Buiting
(Continued)

FOREIGN PATENT DOCUMENTS

DE    36 29 353    1/1988
DE    40 34 611    5/1992
(Continued)

OTHER PUBLICATIONS

Japanese Examination Report Translation; Feb. 7, 2013; 2 pages.

*Primary Examiner* — Justine Yu
*Assistant Examiner* — Colin W Stuart
(74) *Attorney, Agent, or Firm* — Knobbe, Martens, Olson & Bear, LLP

(57) ABSTRACT

A humidifier and humidity sensor is disclosed for use with a breathing assistance apparatus. The humidity sensor preferably includes means to sense absolute humidity, relative humidity and/or temperature at both the patient end and humidifier end. The humidifier may also include provision to both control independently the humidity and temperature of the gases. Further, a chamber manifold is disclosed to facilitate easy connection of the humidifier to various outlets, inlets and sensors. A heated conduit is described which provides a more effective temperature profile along its length.

20 Claims, 4 Drawing Sheets

Related U.S. Application Data division of application No. 10/686,460, filed on Oct. 15, 2003, now Pat. No. 7,146,979, which is a division of application No. 09/808,567, filed on Mar. 14, 2001, now Pat. No. 6,918,389.

(51) Int. Cl.
   *A61M 16/00* (2006.01)
   *A61M 16/10* (2006.01)

(52) U.S. Cl.
   CPC ...... *A61M 16/0883* (2014.02); *A61M 16/109* (2014.02); *A61M 16/1075* (2013.01); *A61M 16/1095* (2014.02); *A61M 16/16* (2013.01); *A61M 16/162* (2013.01); *A61M 2016/003* (2013.01); *A61M 2016/102* (2013.01); *A61M 2205/50* (2013.01)

(58) Field of Classification Search
   USPC .......... 128/203.17, 203.16, 203.26, 203.27,128/203.12, 203.15, 204.14, 204.17, 204.18; 261/130, 142, 119.1, DIG. 65, DIG. 46
   See application file for complete search history.

(56) References Cited

U.S. PATENT DOCUMENTS

| | | | |
|---|---|---|---|
| 3,584,193 A | 6/1971 | Badertscher | |
| 3,695,267 A | 10/1972 | Hirtz et al. | |
| 3,766,914 A | 10/1973 | Jacobs | |
| 3,914,349 A | 10/1975 | Stipanuk | |
| 4,013,122 A | 3/1977 | Long | |
| 4,013,742 A | 3/1977 | Lang | |
| 4,038,980 A | 8/1977 | Fodor | |
| 4,051,205 A | 9/1977 | Grant | |
| 4,060,576 A | 11/1977 | Grant | |
| 4,110,419 A | 8/1978 | Miller | |
| 4,172,105 A | 10/1979 | Miller et al. | |
| 4,500,480 A | 2/1985 | Cambio, Jr. | |
| 4,529,867 A | 7/1985 | Velnosky et al. | |
| 4,574,188 A | 3/1986 | Midgley et al. | |
| 4,640,804 A | 2/1987 | Mizoguchi | |
| 4,676,237 A | 6/1987 | Wood et al. | |
| 4,684,786 A | 8/1987 | Mann et al. | |
| 4,710,887 A | 12/1987 | Ho | |
| 4,722,334 A | 2/1988 | Blackmer et al. | |
| 4,753,758 A | 6/1988 | Miller | |
| 4,780,247 A | 10/1988 | Yasuda | |
| 4,829,781 A * | 5/1989 | Hitzler | 62/311 |
| 4,829,998 A | 5/1989 | Jackson | |
| 4,911,157 A | 3/1990 | Miller | |
| 4,911,357 A | 3/1990 | Kitamura | |
| 4,921,642 A | 5/1990 | LaTorraca | |
| 4,941,469 A | 7/1990 | Adahan | |
| 5,031,612 A | 7/1991 | Clementi | |
| 5,062,145 A | 10/1991 | Zwaan et al. | |
| 5,092,326 A | 3/1992 | Winn et al. | |
| 5,101,820 A | 4/1992 | Christopher | |
| 5,148,801 A | 9/1992 | Douwens et al. | |
| 5,224,923 A | 7/1993 | Moffett et al. | |
| 5,231,979 A | 8/1993 | Rose et al. | |
| 5,336,156 A | 8/1994 | Miller et al. | |
| 5,346,128 A | 9/1994 | Wacker | |
| 5,367,604 A | 11/1994 | Murray | |
| 5,388,443 A | 2/1995 | Manaka | |
| 5,392,770 A | 2/1995 | Clawson et al. | |
| 5,404,729 A | 4/1995 | Matsuoka et al. | |
| 5,454,061 A | 9/1995 | Carlson | |
| 5,482,031 A | 1/1996 | Lambert | |
| 5,492,676 A * | 2/1996 | Katatani et al. | 422/168 |
| 5,516,466 A | 5/1996 | Schlesch et al. | |
| 5,529,060 A | 6/1996 | Salmon et al. | |
| 5,558,084 A | 9/1996 | Daniell et al. | |
| 5,564,415 A | 10/1996 | Dobson et al. | |
| 5,588,423 A | 12/1996 | Smith | |
| 5,640,951 A | 6/1997 | Huddart et al. | |
| 5,673,687 A | 10/1997 | Dobson et al. | |
| 5,759,149 A | 6/1998 | Goldberg et al. | |
| 5,769,071 A | 6/1998 | Turnbull | |
| 5,906,201 A | 5/1999 | Nilson | |
| 5,943,473 A | 8/1999 | Levine | |
| 5,988,164 A | 11/1999 | Paluch | |
| 5,991,507 A | 11/1999 | Bencsits | |
| 6,024,694 A | 2/2000 | Goldberg et al. | |
| 6,050,260 A | 4/2000 | Daniell et al. | |
| 6,078,730 A | 6/2000 | Huddart et al. | |
| 6,095,505 A | 8/2000 | Miller | |
| 6,125,847 A | 10/2000 | Lin | |
| 6,158,431 A | 12/2000 | Poole | |
| 6,189,870 B1 | 2/2001 | Withall | |
| 6,311,958 B1 | 11/2001 | Stanek | |
| 6,349,722 B1 | 2/2002 | Gradon et al. | |
| 6,367,472 B1 | 4/2002 | Koch | |
| 6,394,084 B1 | 5/2002 | Nitta | |
| 6,397,841 B1 | 6/2002 | Kenyon et al. | |
| 6,397,846 B1 | 6/2002 | Skog et al. | |
| 6,398,197 B1 | 6/2002 | Dickinson et al. | |
| 6,463,925 B2 | 10/2002 | Nuckols et al. | |
| 6,474,335 B1 | 11/2002 | Lammers | |
| 6,543,412 B2 | 4/2003 | Amou et al. | |
| 6,564,011 B1 | 5/2003 | Janoff et al. | |
| 6,694,974 B1 | 2/2004 | George-Gradon et al. | |
| 6,718,974 B1 | 4/2004 | Moberg | |
| 6,918,389 B2 | 7/2005 | Seakins et al. | |
| 8,091,547 B2 | 1/2012 | Thudor et al. | |
| 8,235,041 B2 * | 8/2012 | Seakins | A61M 16/08 128/203.26 |
| 2002/0124847 A1 | 9/2002 | Smith et al. | |
| 2002/0186966 A1 | 12/2002 | Zimmer et al. | |

FOREIGN PATENT DOCUMENTS

| | | |
|---|---|---|
| DE | 33 11 811 | 10/1994 |
| DE | 94 09 231.1 | 12/1994 |
| EP | 0 258 928 | 9/1988 |
| EP | 0 481 459 | 4/1992 |
| EP | 0 556 561 | 8/1993 |
| EP | 616 166 | 9/1994 |
| EP | 0 672 430 | 9/1995 |
| EP | 0 885 623 | 12/1998 |
| EP | 1 138 341 | 10/2001 |
| GB | 1 167 551 | 10/1969 |
| GB | 2 277 689 | 11/1994 |
| JP | 05-317428 | 12/1993 |
| JP | 08-061731 | 3/1996 |
| JP | 09-234247 | 9/1997 |
| JP | H09-234247 | 9/1997 |
| JP | H09-276408 | 10/1997 |
| JP | 2001-129091 | 5/2001 |
| SU | 379270 | 4/1973 |
| WO | WO 98/26826 | 6/1998 |
| WO | WO 01/10489 | 2/2001 |
| WO | WO 02/32486 | 4/2002 |

* cited by examiner

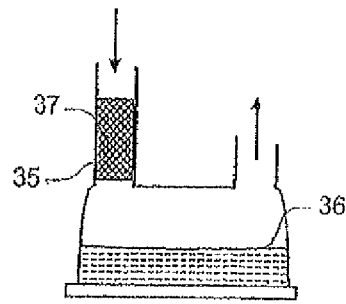
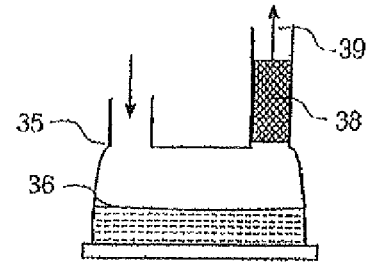
FIGURE 7          FIGURE 8
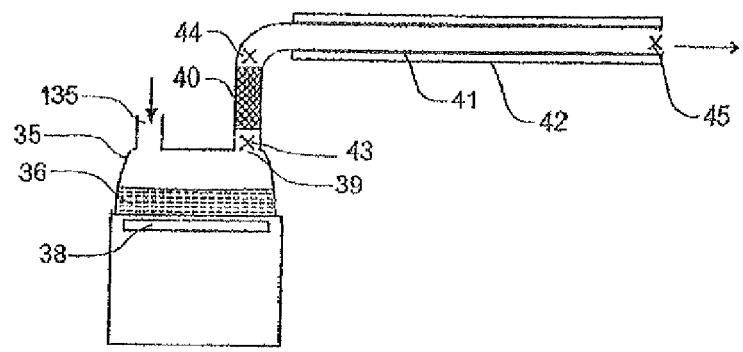
FIGURE 9
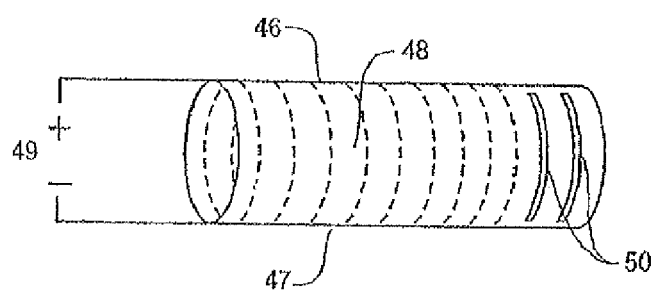
FIGURE 10

BREATHING ASSISTANCE APPARATUS

CROSS-REFERENCE TO RELATED APPLICATIONS

This application is a continuation of U.S. patent application Ser. No. 11/554,792, filed Oct. 31, 2006 now U.S. Pat. No. 8,235,041, which is a divisional of U.S. patent application Ser. No. 10/686,460, filed on Oct. 15, 2003, now U.S. Pat. No. 7,146,979, issued on Dec. 12, 2006, which is a divisional application of U.S. patent application Ser. No. 09/808,567, filed on Mar. 14, 2001, now U.S. Pat. No. 6,918,389, issued on Mar. 3, 2005, which claims priority to New Zealand Application No. 503495, filed Mar. 21, 2000.

BACKGROUND OF THE INVENTION

Field of the Invention

The present invention relates to the use of an humidification system particularly, but not solely, for providing respiratory assistance to patients receiving mechanical ventilation or respiratory support.

Description of the Related Art

A number of methods are known in the art for supplying humidified gases to a patient requiring breathing assistance. Such prior art humidifiers generally comprise a source of pressurised air (or other mixture of gases), a humidification chamber including a source of water and a heating means to vaporise the water, and a conduit to convey the humidified gases to the patient or user.

For example U.S. Pat. No. 4,038,980 describes a "flash vaporisation" humidifier where water drips onto a low thermal mass heater to create respiratory humidity. It mentions "control means may be provided automatically to regulate the water supply rate in response to means sensing the relative humidity", however they prefer a manual control of water flow rate. Thus it incorporates a humidity sensor and controls the water rate, as opposed to controlling the amount of electrical heating.

U.S. Pat. No. 5,092,326 also describes the use of a humidity sensor in a humidifier. It describes a high frequency ventilation system that incorporates a heated humidifier and a humidity sensor, where these are linked to a central microprocessor. Apparatus is disclosed to moisten a gas mixture supplied to the airway, and a microprocessor controls the amount of moisture supplied to the gas mixture. While it discloses a humidity sensor at the patient airway, it doesn't describe the actual humidification configuration to be used.

U.S. Pat. No. 5,769,071 describes a humidifier incorporating a heat and moisture exchanger (HME), supply of water to the HME, heater element and humidity sensor. The humidity sensor can control humidity via water supply rate or temperature (via the heater element). Also the humidity sensor is described as being at the patient airway U.S. Pat. No. 5,988,164 describes a heated breathing tube system for use with a humidifier. This uses a relative humidity sensor (located near the patient) to control the amount of heating provided by the heated breathing circuit so that the gas is at a constant level of relative humidity. The heated breathing circuit may use either electrical heating, or heating via warm recirculating water in a tube. Also described is a method of control of the electric heater wire or heated water tube based on the output of relative humidity sensor.

The previously mentioned U.S. Pat. Nos. 4,038,980 and 5,769,071 both describe humidifiers where the humidification chamber is located close (proximal) to the patient. These have the disadvantage of introducing weight, heat and complexity near the patient which is inconvenient and could be painful to the patient. Of the cited prior art only U.S. Pat. No. 5,988,164 specifically describes the humidification chamber as being located remotely from the patient.

There are several disadvantages of the prior art systems using a humidification chamber located remotely from the patient. It is normally assumed that gases leaving such prior art humidifiers are saturated with water vapour (100% relative humidity). However there is no guarantee that the gases leaving such humidifiers are in fact saturated with water vapour. In certain circumstances (e.g. with the incoming air already warm), the gases leaving such humidifiers can be significantly less than 100% relative humidity. This is because as they are typically controlled to achieve a desired outlet gas temperature, which in such cases may not be much more than the incoming air.

Another drawback of the prior art systems is that condensation can occur in the (sometimes heated) conduits connecting the patient to the respiratory assistance equipment. This may occur if the temperature profile along such conduits is not even and allows some parts of the conduit to be colder than the gas at these points.

A third disadvantage of such prior art systems is where the gas leaving the humidifier is at 100% relative humidity it must be heated immediately by some form of conduit heater or it may lose heat through the walls of the conduit, which results in condensation and therefore a drop in the amount of absolute humidity contained in the gas.

Another fourth disadvantage of the prior art systems is the need for a sensor very near to the patient, which adds to the weight and bulk of equipment at the patient's airway.

A fifth disadvantage of the prior art systems is that intermittent or varying flow rates will cause the absolute humidity that is generated by the humidifier to be uneven. This is because the flow rate is varying faster than any control loop that might operate in such humidifiers. Air which passes through the humidifier at a high flow rate has had little time to be heated and humidified, while air that passes through the chamber at a low flow rate will be hotter and contain higher absolute humidity. Consequently it is difficult for a conduit in such prior art systems to transport these high humidity boluses without condensation and consequent loss of absolute humidity.

SUMMARY OF THE INVENTION

It is therefore an object of the present invention to provide a humidification system which goes some way to overcoming the above mentioned disadvantages, or which will at least provide the public with a useful choice.

Accordingly in a first aspect the present invention consists in a humidification apparatus for humidifying gas for a patient or other person in need of such gas comprising: an inlet receiving gas, an outlet providing gas with a predetermined humidity and/or temperature, a humidifier configured to provide water vapour to said gas passing through said humidification apparatus, an air heater configured to directly heat said gas passing through said humidification apparatus in parallel to said humidifier, at least one sensor configured to provide an indication of at least two of, relative humidity, absolute humidity and temperature, a controller or processor configured to energise said humidifier and said air heater to achieve a predetermined combination of any two of absolute humidity, relative humidity and temperature.

Wherein said sensor comprises an absolute humidity sensor for providing an indication of the absolute humidity of said gas at least one point in the flow path through said apparatus of said gas, and said humidifier including a body of liquid water.

Wherein said humidifier comprises a metal spiral element to heat said body of water.

Wherein said humidifier comprises a heated porous ceramic member adapted to be in contact with said body of water and said gas.

Wherein humidifier comprises a heated semipermeable membrane adapted to be in contact with said body of water and said gas.

Wherein said air heater having a humidification bypass, for allowing a portion of said gases to flow to pass from said inlet to said outlet substantially without humidification.

Wherein said humidification bypass includes a bypass conduit in at least partially passing through said body of water for conveying a portion of said gas from said inlet to said outlet, and a valve provided in said bypass conduit to thereby restrict of the portion of said gas in said bypass conduit, the gas flowing through said bypass conduit being heated by the surrounding said body of water.

Wherein said humidification bypass further having a bypass conduit for conveying a portion of said gas from said inlet to said outlet including a bypass heater adapted to heat the portion of said gas in said bypass conduit and/or said bypass conduit, and a valve provided in said bypass conduit to thereby restrict the portion of said gas in said bypass conduit.

Wherein the restriction provided by said valve on the portion of said gas in said bypass conduit is in use permanently set.

Wherein the restriction provided by said valve on the portion of said gas in said bypass conduit is in use manually adjustable.

Wherein a humidification apparatus further comprises a flow sensor providing an indication of the instantaneous flow rate of wherein said control configured to control the restriction provided by said valve on the flow rate of the portion of said gases flow in said bypass conduit based on said indication of instantaneous flow rate of said gases flow through said humidifier, in order that the gases flow exiting from said humidifier is of substantially constant humidity.

Wherein said valve comprising an electromechanical actuator connected to a valve member wherein the energisation of said electromechanical actuator varies the position of said valve member thereby varying the restriction provided by said valve on the flow rate of the portion of said gas in said bypass conduit.

Wherein said valve comprising either a valve member connected to an elastic member or an elastic valve member wherein said valve being positioned in said gases flow at said inlet and the position of said valve member or said elastic valve member thereby determines the portion of said gas in said bypass conduit.

Wherein the position of said valve member or said elastic valve member providing an indication of the rate of flow of said gas at said inlet.

Wherein a humidification apparatus further comprises a conduit to convey said gas from said outlet to a patient including insulation adapted to minimise the rate of heat energy lost by said gas in said conduit, said controller adapted to energise said humidifier and said air heater to minimise the condensation of the vapour from said gases in said conduit while providing predetermined levels of absolute humidity.

In a second aspect a humidification apparatus for humidifying gas for a patient or other person in need of such gas comprising: an inlet receiving gas, an outlet providing gas with a predetermined humidity and/or temperature, an air heater adjacent to said inlet for heating of said flow of gas, a humidifier configured to provide water vapour to said gas passing from said heater to said outlet, in series with said heater, at least one sensor configured to provide an indication of at least two of, relative humidity, absolute humidity and temperature, a controller or processor configured to energise said humidifier and said air heater to achieve a predetermined combination of any two of absolute humidity, relative humidity and temperature.

Wherein said air heater comprises a heater wire in a conduit connected to said inlet.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples.

BRIEF DESCRIPTION OF THE DRAWINGS

One preferred form of the present invention will now be described with reference to the accompanying drawings in which;

FIG. 7 shows a chamber where the dry gas entering chamber is preheated, FIG. 8 shows a chamber where the dry gas entering chamber is heated after leaving the chamber, FIG. 9 shows a chamber combined with an unheated, well insulated delivery tube, FIG. 10 shows construction of a tube incorporating flexible PTC elements in a parallel wire configuration.

DETAILED DESCRIPTION OF THE PREFERRED EMBODIMENT

Figure 1:
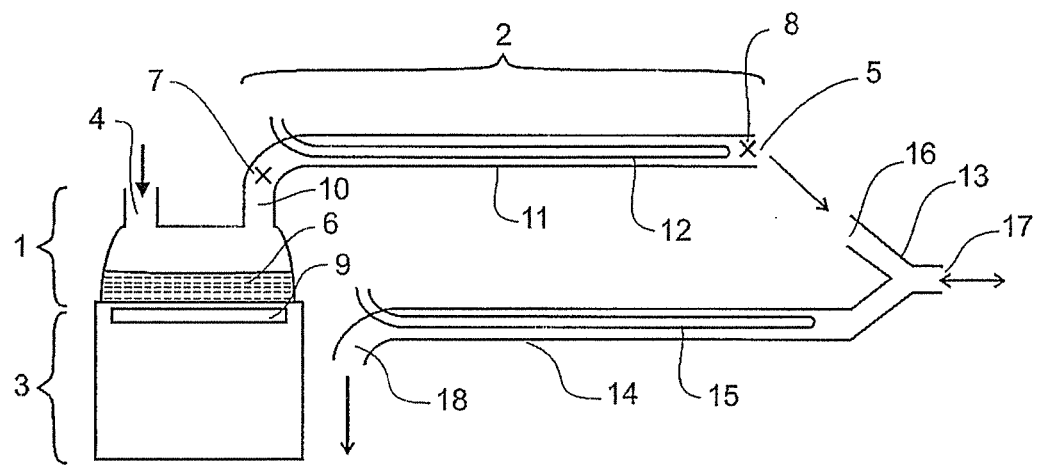
FIG. 1 shows an example of an humidification system, comprised of three parts.

FIG. 1 illustrates a typical respiratory humidification system, comprised of three parts:

1) a humidification chamber located at a distance from the patient, which heats and substantially saturates gases flowing through it;

2) a delivery system consisting of a flexible tube which carries humidified gases from the humidification chamber 1 to the gas outlet 5; and 3) a heater base 3 which heats the humidification chamber 1 and provides measurement and control functions.

The gas to be humidified flows into the chamber 1 from port 4 and leaves the delivery system 2 at gas exit port 5. Gas from exit port 5 flows to a patient via a face mask or similar (not shown). The system is controlled using sensors located at positions 7 and 8—typically temperature probes. Dry gases at the gas input 4 are heated and humidified by passing over the surface of hot water 6 in the chamber 1 so that they are substantially saturated with water vapour when they leave chamber 1 at exit port 10. Hot water 6 is heated by heater plate 9 and the amount of heating is controlled so that the gas reaches a predetermined temperature at exit port 10. This temperature is measured by sensor 7. Therefore the humidification chamber 1 acts to heat and humidify the medical gases so that they are substantially saturated at the output of chamber 1, and are at a predetermined temperature.

The gas delivery system 2 (also known as a delivery tube or breathing circuit) consists of a flexible tube 11 containing a heater 12, which may consist of a heated resistance wire. The gas from the humidification chamber 1 passes through the tube 11 and is heated by heater 12 to offset heat losses through the walls of tube 11. The amount of heating applied to heater 12 is regulated so that the gas reaches a predetermined temperature at gas outlet 5, as measured by sensor 8. The control temperature at sensor 8 is usually higher than the control temperature at sensor 7, so that the gas is heated along tube 11 to ensure that condensation doesn't occur in the tube.

The system as described has gas entering gas inlet 4 from a continuous flow gas source (not shown) and exiting the system through gas outlet 5. However the system is equally applicable where the gas source is a ventilator, which creates intermittent flow patterns to provide breaths to a patient. In this case gas outlet port 5 is connected directly to gas inlet port 16. The patient is connected to port 17 via an endotracheal tube or similar (not shown). During patient inspiration dry gases from the ventilator enter the system at inlet port 4, pass through chamber 1, delivery system 2, pass through wye-piece 13 and reach the patient through port 17. During patient exhalation gases pass back through port 17, through wye-piece 13, tube 14 and leave through gas outlet port 18. Tube 14 may also be heated by heater 15 to prevent condensation.

Absolute Humidity Sensing

Humidifiers incorporating humidity sensors for display or control have been described in the prior art, however all used humidity sensors which were positioned at the patient airway. The current work describes novel humidifier configurations incorporating a humidity generating chamber located at a position which is remote from the patient, a heated breathing circuit to transfer humidity to the patient, and humidity sensors to control the level of absolute or relative humidity supplied to the patient. These humidity sensors are to be located either: 1) at the chamber outlet only, 2) at both the chamber outlet and near the patient, or 3) near the patient only.

One aspect of the present invention would be to use a humidity sensor as sensor 7. The purpose of humidity sensor 7 is to determine the absolute amount of humidity which is being generated by chamber 1. Accordingly an absolute humidity sensor would be ideal for use as sensor 7, although the use of a relative humidity sensor with associated temperature sensor could equally be used. This system has the advantage of creating a controlled level of absolute humidity at chamber outlet 10, however this level of absolute humidity may not reach the patient if condensation is allowed to occur in tube 11.

An alternative system which would overcome this disadvantage is to use a second absolute humidity sensor at point 8 instead of a temperature sensor. The difference in absolute humidity between sensors 7 and 8 allows the humidifier to determine whether condensation is occurring between the two points. If the two absolute humidity sensors 7 and 8 read the same level of absolute humidity then no condensation is occurring in the tube. If the absolute humidity at sensor 7 is greater than at sensor 8, then the difference shows the rate of condensation that is occurring.

One control strategy would be to control the amount of heating provided to heater 12 so that the absolute humidity difference is reduced to zero. However the tube may still contain mobile condensate because the humidity difference only describes the rate of condensation, not the absolute amount of condensate in the tube. Another control strategy is to remove this condensate and hence create a dry tube by heating heater 12 so that the rate of measured condensation is negative (i.e. condensation is being evaporated in tube 11) until the measured condensation rate reaches zero, indicating that all of the condensate has been removed. The amount of heating can then be reduced until the sensors show that condensation has just started to occur, then the heating can be increased slightly to the optimum level. Drying out of the tube may be a continuous process, or may be initiated at regular time intervals.

Another variation of the system shown in FIG. 1 would be to use a temperature sensor for sensor 7 and an absolute humidity sensor at point 8. This system is simpler than having an absolute humidity at both points 7 and 8. In operation the controller would have to adjust the amount of heating at heater 12 and heater plate 9 so that the correct level of absolute humidity was reached without condensate in delivery tube 12. In practice two separate control algorithms would be required, one to control the amount of heating occurring in tube 11 so that no condensation occurred, and another to control heater plate 9 so that the desired level of absolute humidity was generated in chamber 1. The two algorithms could work concurrently because the heater plate 9 will respond slower than heater 12, so quick changes in absolute humidity would indicate the action of heater 12. Sensor 7 provides a control point for heater plate 9, but may not be needed.

Low Relative Humidity Chambers

All systems described so far have used a chamber 1 which attempts to humidify the gas leaving gas outlet 10 to a high level of relative humidity. While this condition isn't essential for the correct operation of the new humidification configurations just described because they use humidity control, it was essential for the prior art humidifier where control is purely based on temperature. However there are some advantages to be gained from using a chamber which heats gases to the correct absolute humidity, but at a low relative humidity (i.e. the temperature of the gas is higher than the dewpoint of the gas, therefore the gas is not saturated).

The first advantage is that it is easier to design a heated delivery system to transport such a gas without condensation, since the gas doesn't need to be heated immediately after it enters the delivery tube to prevent condensation. Secondly, the use of low relative humidity gases leaving the chamber means that the heater element 12 can be rated at a lower power than would otherwise be the case, as the gas already has a higher energy content and can tolerate a greater loss of energy before the gas condenses in the tube 12. It may even be possible to use an unheated, well insulated breathing circuit instead of a heated breathing circuit if the chamber provides gas with enough energy. Note that low relative humidity chambers can only be used if the heating to the chamber is controlled using an absolute humidity sensor, not a temperature sensor, since otherwise the absolute humidity output would be too low.

Figure 2:
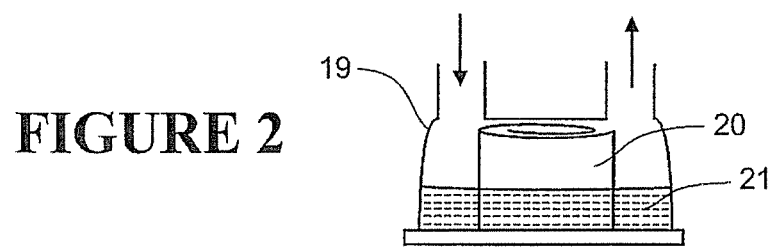
FIG. 2 shows a chamber which incorporates a metal element.

To this end, some humidification chamber configurations which provide a high temperature, low relative humidity gas output are shown in FIGS. 2-8. FIG. 2 shows a chamber which incorporates a metal element 20 (e.g. a spiral scroll shape), but without wicking paper attached. This provides both dry heating (via the metal element) and heated humidification from the heated water 21. With this configuration the chamber 19 provides gas which is not saturated because some of the heating provided to the gas is dry heating via the metal scroll. The relative humidity generated by the chamber is affected by the gas flow path, scroll shape, dimensions, and the water level, and so is not readily adjustable in use. However chamber 19 does give the condensate reducing advantages provided by a low relative humidity, controlled absolute humidity output.

Figure 3:
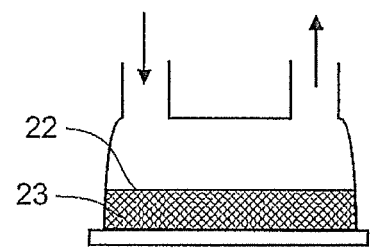
FIG. 3 shows a chamber using a porous material to provide a heating and humidifying function.
Figure 4:
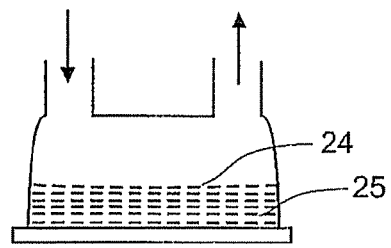
FIG. 4 shows a chamber using a semipermeable membrane.

FIGS. 3 and 4 are alternative humidification chambers which provide low relative humidity, high temperature gases at their output. FIG. 3 shows a chamber using a porous material 22 (such as a porous ceramic) containing water 23 to provide a heating and humidifying function, while FIG. 4 shows a chamber using a semipermeable membrane 24 to provide a barrier to the water 25 in the chamber. In both cases these chambers provide dry heating via the porous or semipermeable material, as well as heated humidification from the water. In both cases the ratio of heating to humidifying is fixed and cannot be easily adjusted except by limiting the water supply.

Figure 5:
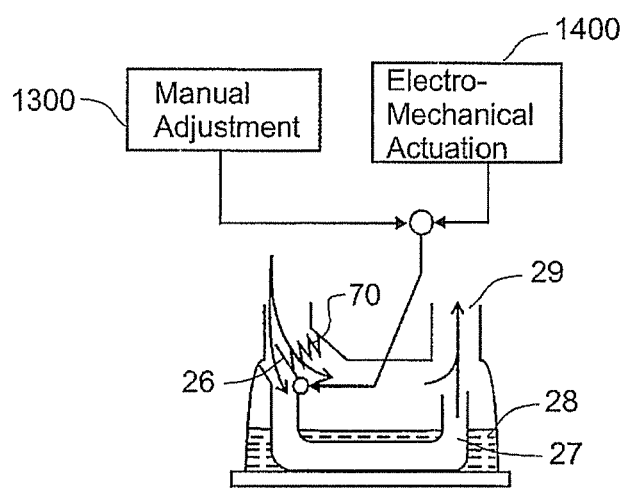
FIG. 5 shows a chamber with a variable valve to adjust the ratio of gas which are bypassed.

FIGS. 5 to 8 show chambers that can supply gases at varying levels of relative humidity and temperature. In FIG. 5 a variable valve 26 allows us to adjust the ratio of gas which passes through the dry bypass tube 27 to that which flows across the surface of the water 28. The bypass tube passes under the water to heat the gas. The two gas streams merge at the output 29. This is an example of a "parallel" system where the gas splits and takes two different paths to provide heating and humidification. In FIG. 6 the gas is again split into two gas paths using an adjustable valve 30. One part of the gas gets humidified by passing across the water 31 in chamber 32, while the other is heated by heater 58, which surrounds tube 33. The gas paths merge at junction 34.

Figure 6:
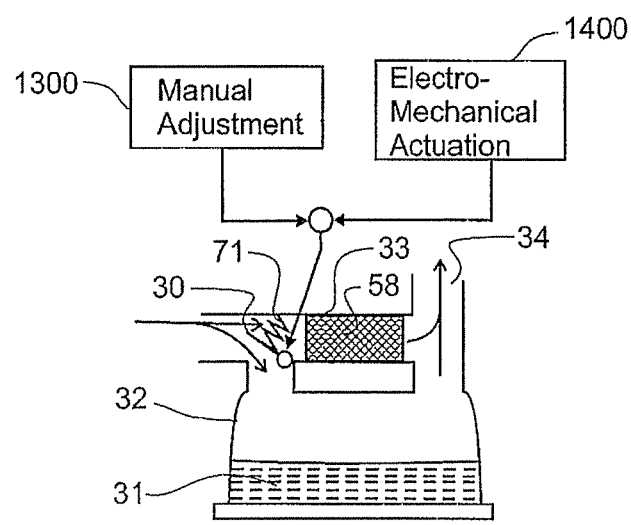
FIG. 6 shows a chamber with an adjustable valve 30 where one part of the gas gets humidified while the other is heated.

The angle of variable valves 26 and 30 in FIGS. 5 and 6, may be permanently set, may be manually adjustable 1300, or may be automatically adjustable for example by electro-mechanical actuation 1400. One advantage of an automatically adjustable valve would be to provide a constant level of humidity out of the chamber when used with intermittent flow rates, for example when used with a ventilator. These flow patterns can be a problem because parts of the breath cycle contain less humidity than other parts, due to the chamber providing less humidity at higher flow rates. One way to overcome this problem is to measure the instantaneous flow rate using a fast response flow sensor, and then rapidly adjusting the angle of the variable valve. A more practical method of achieving this effect would be to spring-load valves 26 and 30 using springs 70 and 71 or use an elastic valve member to form the variable valve. This would mean that low flow rates would mostly pass through the bypass tubes, while high flow rates would operate the spring-loaded valve and allow more gas to pass across the water in the humidification chamber. The angle of the spring-loaded variable valve could also be used by the humidifier to measure the gas flow rate.

FIGS. 7 and 8 show alternative series configurations for low relative humidity chambers, where the dry gas entering chamber 35 containing heated water 36 is either pre-heated via heater 37 in FIG. 7, or heated via heater 38 in FIG. 8 after leaving the chamber. In both cases the heater provides dry heating to the gas and results in a low relative humidity, high temperature gas leaving outlet 39.

Any of the low relative humidity, high temperature chambers shown in FIGS. 2 to 8 can be used in conjunction with the humidity control schemes described previously in this patent, but not successfully with the prior art humidifier due to it being temperature controlled, not humidity controlled.

Insulated Delivery Tube

Another facet of the invention is shown in FIG. 9. Here the low relative humidity, high temperature humidification system from FIG. 8 has been combined with an unheated, well insulated delivery tube. The incoming gas enters at port 135 into the standard humidification chamber 35 containing water 36 which is heated by heater plate 38. The gas is substantially saturated in the chamber then leaves the chamber through gas outlet 39 and enters heated tube section 40 which heats the humid gas to a higher temperature, so that it has a low relative humidity. The gas then passes through tube 41 which has an insulating layer 42 around it. Preferably the insulating layer is a thin jacket of stagnant air which reduces heat loss. As the high temperature gas, low relative humidity gas passes through the insulating tube, a small amount of heat is lost through the tube walls, and therefore the gas cools. However the amount of heating applied to heater 40 is controlled, so that the gas is never allowed to cool below its dewpoint, which would result in condensation within tube 41.

Several different sensor configurations are proposed. Firstly, sensor 43 could be an absolute humidity sensor which controls heater plate 38 so that chamber 36 produces the desired level of humidity. In one embodiment sensor 45 is a temperature sensor, which controls heater 40 so that the gas passing sensor 45 remains at a certain desired temperature. If this temperature is greater than the dewpoint of the gas at sensor 43, then condensation should not occur in tube 41. However there may already be condensate in tube 41 when the humidifier is turned on. If a humidity sensor is used for sensor 45 instead of a temperature sensor, then the level of condensate occurring in the tube 41 can be controlled. The algorithms described earlier in this patent for dual-humidity sensor control can be used with this system.

An alternative location for the absolute humidity sensor is at position 44 instead of 43. The absolute humidity here should be the same as at 43 because the gas has been heated and so hasn't lost any moisture. However there may be advantages to placing the absolute humidity sensor at 44, for instance due to better sensor operation in a low relative humidity environment. This location for the absolute humidity sensor can be used with either a temperature or absolute humidity sensor at location 45.

Humidifier Configurations Without any Patient Airway Sensors

Yet another aspect of this patent relates to removing the need for a sensor at the patient airway. To remove this sensor safely, we must be certain that the gas entering the delivery tube has a safe level of temperature and absolute humidity, and that the surfaces inside the delivery tube do not exceed safe temperature levels. This implies a delivery tube that has a constant internal wall temperature.

It would be desirable, therefore, to have a heated delivery tube which self-regulates its temperature at a desired level. The heater could either be embedded in the wall of the delivery tube itself, or it could lie inside the lumen of the delivery tube, or it could be wrapped around the outside of the delivery tube. Such a heater could be made from positive temperature coefficient (PTC) material (such as "Winterguard" from Raychem Corp., Menlo Park, Calif. USA), so that the resistance of the heater increases if the heater is hot, resulting in reduced power. However the delivery tube may pass through more than one environment, or may have localised drafts present on certain parts of the tube. If the PTC elements are arranged in parallel, then the full benefit of the PTC heater can be envisaged. If the PTC elements are arranged in parallel, then the cold portions of the tube will have a lower resistance, which will result in more heat being dissipated. Thus the tube will tend to regulate its own temperature.

FIG. 10 shows construction of a tube incorporating flexible PTC elements in a parallel wire configuration. The tube 48 is made of a flexible PTC material, which has two low resistive strip connections, 46 and 47, on either side of it. This allows each portion of the tube to consist of short conducting segments of tube connected in parallel between conductors 46 and 47. These segments are represented by dotted lines encircling the tube in FIG. 10. The conductors 46 and 47 are connected to adjustable voltage source 49, which may be AC or DC. The tube would have an outer layer (not shown) which provides electrical insulation and thermal insulation to the tube. Each longitudinal segment of the tube will be able to regulate its own temperature independently of the rest of the tube. To enhance this operation, it may be necessary to provide parallel slots 50 running perpendicular to the axis of the tube, to eliminate electrical cross-connection between the different PTC segments.

Although one specific PTC heated tube design has been envisaged and described, other PTC tube designs could be used. It may also be of advantage to create a PTC tube that has a differing temperature profile along its length rather than a constant temperature profile. The PTC design could also be extended to incorporate PTC heaters in other parts of the patient breathing circuit, such as the flexible extension tube which is usually connected between the Y-piece (port 17 of FIG. 1) and the patient's endotracheal tube. A further extension of the PTC tube concept would be into a self-heated and temperature controlled endotracheal tube.

Figure 11:
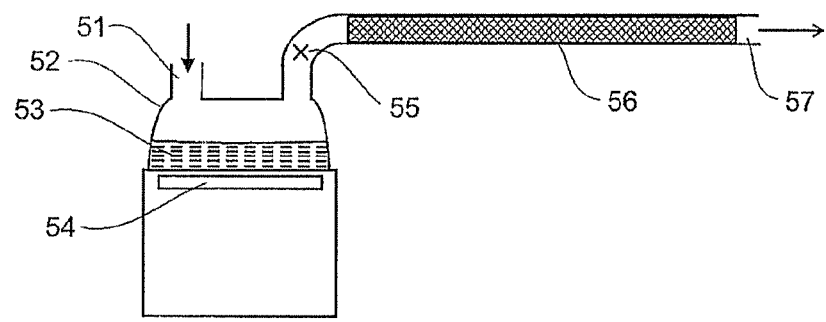
FIG. 11 shows a humidifier configuration using the tube in FIG. 10.

The PTC tube described in FIG. 10 allows us to create a humidifier which doesn't use any sensor at the patient airway. FIG. 11 shows a humidifier configuration using this tube. Gas enters humidification chamber 52 via inlet port 51 and is humidified by water 53, heated by heater plate 54. Absolute humidity sensor 55 controls the heater plate so that the gas passing sensor 55 is at a desired level of absolute humidity. PTC tube 56 is heated by an external voltage (not shown) so that the internal surface temperature is at a constant desired temperature, which is selected to be above the dewpoint of the gas. The gas which leaves tube 56 at outlet 57 will therefore be near the temperature of the tube, and containing the desired level of absolute humidity which was controlled by absolute humidity sensor 55.

A variation of the system shown in FIG. 11 would be to use a temperature sensor at position 55. Another variation of a tube with a constant internal wall temperature would a delivery tube with heated water or other fluid pumped through smaller conduits in the wall of the delivery tube. Since the heated fluid has a high specific heat relative to air, the temperature of the fluid remains fairly constant during passage through the delivery wall conduits.

Use of a Sensor/Heater Manifold

Traditional humidifiers have tended to use sensors that are probe shaped, so that they can be inserted through specifically designed holes in the side of the breathing circuit to measure temperature. However the humidifier configurations that have been described in this patent incorporate many sensors around the chamber, so the use of a manifold 59 as shown in FIG. 12 may be useful.

Figure 12:
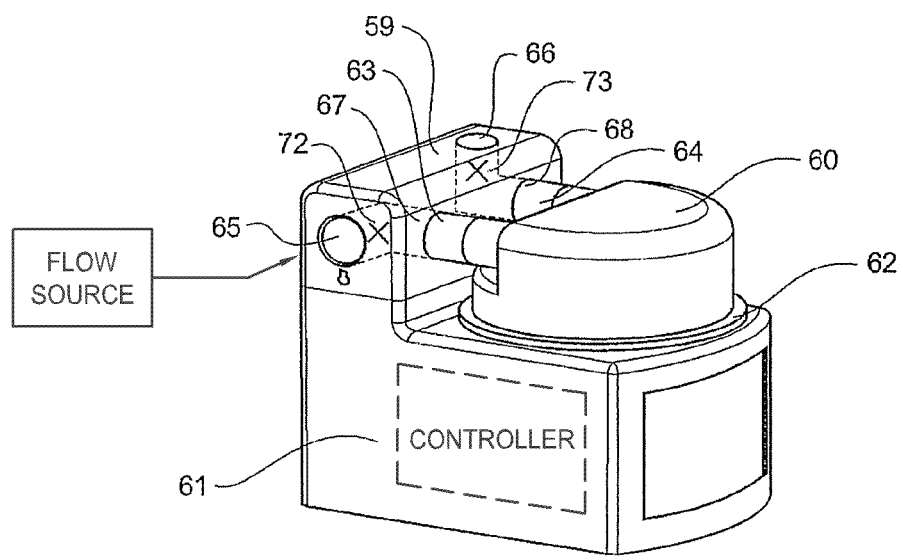
FIG. 12 shows the chamber manifold.

The humidification chamber 60 is a removable item which can be slid onto the humidifier base 61 as shown in FIG. 12. As the chamber 60 is slid onto the humidifier base 61, its base makes contact with heater plate 62 and its inlet and outlet ports 63 and 64 make contact with holes 67 and 68 inside the manifold 59. Dry air to be humidified enters the manifold at port 65, passes out of the manifold through port 67, and flows through port 63 into the chamber 60, where it is humidified.

After leaving chamber 60 the humid gas passes through chamber port 64 into manifold port 68. Finally the humid gas leaves manifold 59 through port 66 and passes to the breathing circuit.

The manifold may be a separate, removable assembly, or it may be an integral part of the humidifier base. It may contain temperature sensors, humidity sensors, flow sensors, or a heater element. These would be located inside the manifold 59 at positions 72 and 73. The manifold 59 may be heated to prevent condensation of humid gas. It could connect to both chamber ports 63 and 64 as described, or it may only connect to the outlet port 64. One advantage of using a manifold is that many sensors or heaters can be combined in a single, cleanable assembly, rather than requiring separate probes which need to be plugged into the breathing circuit. This simplifies connection and setup for the user. Another advantage of a manifold is that the incoming dry gas temperature and flow rate can easily be measured without additional probes and connections.

Variations on the Described Configurations

Although absolute humidity sensors have been described with all of the different humidification schemes described in this patent, relative humidity sensors could also be used. This may involve slightly different control algorithms to the ones described in this patent. Alternatively, a relative humidity sensor could be combined with a temperature sensor. This allows the absolute humidity to be calculated from relative humidity and temperature, rather than being measured directly.

All of the novel humidification schemes that have been described in this patent could be used with additional temperature sensors. These may provide additional benefits such as providing a safety backup in the event of a failed humidity sensor. Another benefit would be maintaining the temperature being delivered to the patient within certain limits so that the relative humidity is not too low, even though the absolute humidity was acceptable.

Similarly it may be useful to measure the air flowrate through the humidifier, as this is an important parameter which affects humidifier control. Therefore flow sensors could be incorporated within any of the previously described systems. One useful prior art flow sensor construction would be to use a sensor based on heat loss from a hot element in the airstream. If a heated humidity sensor is used, the amount of heating that is required for the sensor to achieve temperature can be used to determine the gas flow rate.

Infection control is a prime consideration when designing medical components. To prevent bacterial colonisation of the components in the humidification system, any parts which come in contact with the gas stream could be made out of antibacterial plastic. To prevent contamination of sensor probes, the probe ports could incorporate a disposable sheath which protects the probe from pathogens in the breathing circuit. This would be particularly applicable to temperature probes. In general humidity probes need to have contact with the gas stream so a disposable sheath would be inapplicable to humidity sensors, unless they worked on optical principles, or unless the sheath was made of water vapour permeable material, which did not allow the passage of pathogens. The protective sheath could be an integral part of a disposable breathing circuit.

What is claimed is:

1. A humidification apparatus for humidifying a gases flow to be supplied to a patient or other person comprising:
a humidifier base comprising a heater plate;
a humidification chamber having an inlet and an outlet to allow the gases flow to pass through the humidification chamber from the inlet to the outlet, the humidification chamber being configured to be mounted on the humidifier base in contact with the heater plate;
a removable assembly that connects the humidification chamber to the humidifier base, the removable assembly forming a portion of the humidification apparatus and including a first sensor being supported by the removable assembly, the first sensor being configured to determine a first parameter of the gases flow before the gases flow enters the humidification chamber; and
a controller that controls the heater plate based upon at least the first parameter to heat water in the humidification chamber to humidify the gases flow passing through the humidification chamber.

2. The apparatus of claim 1, wherein the first sensor is located adjacent to the inlet of the humidification chamber when the humidification chamber is mounted on the humidifier base.

3. The apparatus of claim 2, futher comprising a continuous flow gases source.

4. The apparatus of claim 3, wherein the continuous flow gases source is a medical gases supply.

5. The apparatus of claim 1, wherein the first sensor is located upstream of the inlet of the humidification chamber when the humidification chamber is mounted on the humidifier base.

6. The apparatus of claim 1, further comprising a second sensor configured to determine a second parameter of the gases flow.

7. The apparatus of claim 6, wherein the controller is configured to control the heater plate also based on the second parameter.

8. The apparatus of claim 6, wherein at least one of the first and second sensors is a humidity sensor.

9. The apparatus of claim 8, wherein at least one of the first and second sensors is a temperature sensor.

10. The apparatus of claim 1, wherein the removable assembly comprises a manifold.

11. The apparatus of claim 1, wherein the removable assembly comprises at least one gases passageway.

12. A humidification apparatus configured to humidify a flow of gases for delivery to a user, the apparatus comprising:
a flow path of the flow of gases extending from a gases source to a humidification chamber;
the humidification chamber defining a volume configured to contain a volume of liquid;
a heater base comprising a heater configured to heat the volume of liquid, the heater being controlled by a controller; and
a removable assembly that connects the humidification chamber to the heater base, a first sensor mounted to the removable assembly, the first sensor being positioned to sense a property of gases flow before the humidification chamber;
the first sensor being connected to the controller such that the controller is configured to control the heater that is configured to heat the volume of liquid contained within the humidification chamber by adjusting a temperature of the volume of liquid in the humidification chamber based upon output from the first sensor.

13. The apparatus of claim 12, wherein the first sensor is positioned between the gases source and the humidification chamber.

14. The apparatus of claim 12, wherein the first sensor is configured to sense a humidity level of the flow of gases.

15. The apparatus of claim 12, wherein the first sensor is configured to sense a temperature of the flow of gases.

16. The apparatus of claim 12, wherein the removable assembly comprises a manifold.

17. The apparatus of claim 12, wherein the removable assembly comprises at least one gases passageway.

18. A method for humidifying a gases flow to be supplied to a patient or other person comprising:
sensing, using a sensor carried by a removable assembly that connects a humidification chamber to a heater base, the sensor being located on the removable assembly upstream of the humidification chamber, the sensor configured to sense a first parameter of the gases flow inside of the removable assembly prior to the gases flow entering the humidification chamber;
controlling a heater thermally coupled to a volume of liquid in the humidification chamber using output from the sensor located on the removable assembly upstream of the humidification chamber;
transferring water vapor from the volume of liquid to the gases flow passing through the humidification chamber; and
conveying the gases flow out of the removable assembly after the gases flow exits the humidification chamber,
wherein the first parameter is selected from the group consisting of temperature, absolute humidity, relative humidity and flow rate and is used to control the heater in the generation of the water vapor.

19. The method of claim 18, further comprising sensing a second parameter of the gases flow after the gases flow exits the humidification chamber.

20. The method of claim 19, wherein one or more first sensors senses the first parameter and one or more second sensors senses the second parameter, the one or more first sensors being located before the humidification chamber along a flow path of the gases flow through the removable assembly and the one or more second sensors being located after the humidification chamber along a flow path of the gases flow through the removable assembly.

* * * * *

UNITED STATES PATENT AND TRADEMARK OFFICE
CERTIFICATE OF CORRECTION

PATENT NO. : 9,555,210 B2
APPLICATION NO. : 13/540357
DATED : January 31, 2017
INVENTOR(S) : Paul John Seakins et al.

It is certified that error appears in the above-identified patent and that said Letters Patent is hereby corrected as shown below:

In the Specification

In Column 1 at Line 55, after "airway" insert --.--.

In Column 3 at Line 39, change "of wherein" to --of the gas wherein--.

In the Claims

In Column 11 at Line 40, in Claim 3, change "futher" to --further--.

Signed and Sealed this
Eighteenth Day of July, 2017

Joseph Matal
*Performing the Functions and Duties of the*
*Under Secretary of Commerce for Intellectual Property and*
*Director of the United States Patent and Trademark Office*